United States Patent
McIntosh et al.

(10) Patent No.: US 6,998,093 B1
(45) Date of Patent: Feb. 14, 2006

(54) FLUID OXYGENATOR WITH ACCESS PORT

(75) Inventors: Kevin D. McIntosh, Alberville, MN (US); Bruce R. Jones, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/559,452

(22) Filed: Apr. 27, 2000

(51) Int. Cl.
*A61M 1/14* (2006.01)
*A61M 37/00* (2006.01)

(52) U.S. Cl. .................. 422/45; 422/44; 604/6.14; 261/DIG. 28

(58) Field of Classification Search ............ 422/44–48; 604/4.01, 6.14; 261/1, 2, 3, 158, 19, 24, 261/28–9, DIG. 28; 96/4, 10, 11, 243
See application file for complete search history.

(56) References Cited

U.S. PATENT DOCUMENTS

| | | | |
|---|---|---|---|
| 4,111,659 A | 9/1978 | Bowley | |
| 4,424,190 A | 1/1984 | Mather, III et al. | |
| 4,469,659 A | 9/1984 | Carson et al. | |
| RE33,932 E | 5/1992 | Fukasawa et al. | 422/46 |
| 5,312,479 A | 5/1994 | Weinstein et al. | |
| 5,338,770 A * | 8/1994 | Winters et al. | 523/112 |
| 5,358,689 A | 10/1994 | Jones et al. | 422/46 |
| 4,469,659 A | 7/1997 | Carson et al. | |
| 5,667,485 A | 9/1997 | Lindsay | |
| 5,762,869 A * | 6/1998 | White et al. | 422/48 |
| 5,766,480 A | 6/1998 | Cosentino et al. | |
| RE36,125 E | 3/1999 | Haworth et al. | |

FOREIGN PATENT DOCUMENTS

| | | |
|---|---|---|
| EP | 0 089 122 | 2/1983 |
| EP | 0 257 279 | 7/1987 |
| EP | 0 103 899 B1 | 6/1990 |
| WO | 0 705 610 | 10/1994 |

OTHER PUBLICATIONS

A brochure entitled "Medtronic AFFINITY® NT Oxygenation Systems," Clearly the next level of technology, (© Medtronic, Inc. 1999, 6 pp.).
A brochure "Medtronic AFFINITY® NT 511" Instructions For Use brochure, (©Medtronic, Inc. 1999, 53 pp. (Note: p. 6 is blank)).
Medtronic brochure entitled "The Affinity® Hollow Fiber Oxygenator" UC9804380EN 1999.
Medtronic brochure entitled "Minimax Plus™ Oxygenation Systems" UC9605420EN 1998.

* cited by examiner

*Primary Examiner*—Patricia Bianco
(74) *Attorney, Agent, or Firm*—Tom Berry; Jeffrey J. Hohenshell

(57) ABSTRACT

A fluid oxygenating apparatus is provided which includes a housing defining a chamber, a core positioned within the chamber including a fluid channel formed therein, and a bubble release port communicating with the outlet end of the channel. Fluid is flowed through an inlet of the channel and bubbles are released through the bubble release port. A method and system for debubbling a fluid in such an apparatus is also provided.

20 Claims, 5 Drawing Sheets

FLUID OXYGENATOR WITH ACCESS PORT

FIELD OF THE INVENTION

This invention relates to devices that oxygenate and remove carbon dioxide from fluid, including blood. The invention further relates to devices that regulate the temperature of and debubble fluid as it passes through the device.

BACKGROUND OF THE INVENTION

Typical blood oxygenators may be used as artificial cardiorespiratory devices, for example, during cardiopulmonary bypass surgery. Such oxygenators serve as an artificial respiratory system for a patient at a time when the patient is unable to rely on his own respiratory system, e.g. during surgery. These devices act temporarily as a patient's heart and lungs, circulating, adding oxygen to and removing carbon dioxide from a patient's blood while the patient's own heart and lungs are inactive.

It follows that a desirable oxygenator approximates as closely as possible the conditions and components of a patient's respiratory system. Forces mechanically applied to the blood as it flows through the oxygenator, which most closely simulate those normally experienced within the body, are safest and best for the patient's welfare.

Thus, the ambient conditions of existing oxygenators are designed to facilitate careful monitoring during use. For example, the Affinity™ Oxygenation System from Medtronic is clear so that the fluid flowing through the system can be monitored. It is also advantageous that conditions within an oxygenator can be adjusted so that they better resemble those normally experienced in the patient's body. To this end, typical oxygenators may be attached to other components of an oxygenation system, such as adjustable pumps to regulate the flow of blood through the oxygenator or an integrated heater, or cooling device to keep the blood at a desired temperature. Generally, during bypass surgery, the principal blood handling components of an artificial respiratory system would include an oxygenator, an arterial filter and a venous reservoir. These components are generally single-use disposable products.

One condition present in a typical oxygenator that deviates from the normal conditions of the patient's body is the presence of air bubbles in the fluid as it enters the oxygenator. Generally, air is present in an oxygenator before it is used for the first time. This air continues to be present when fluid is first put into the oxygenator and may appear as bubbles in the fluid. Under typical circumstances, the bubbles are removed during the priming of the device. Usually, removal of air bubbles occurs on the distal side of the fiber bundle. Then, any air bubbles on the proximal side must be forced through the fiber bundle to the distal side in order to be removed. Biocompatible coatings and the presence of blood in the device make removal of the air bubbles difficult, as they are unlikely to pass through the fiber wall or through the fiber bundle to the distal side.

These bubbles can cause a number of difficulties in that they may physically obstruct the actual flow of the fluid through the device. The bubbles could also potentially pass through the device and be sent back to the patient, which could cause injury to the patient.

Therefore a means of debubbling the fluid on the proximal side of the fiber bundle is desirable. Furthermore, a means that could be used to access the blood as it enters the oxygenator would be desirable.

SUMMARY OF THE INVENTION

One aspect of the present invention provides a fluid oxygenating apparatus or oxygenator which includes a housing defining a chamber, a core within the chamber, the core including a channel, and a bubble release port communicating with the channel. This oxygenator may be arranged so that fluid may be flowed through the channel and bubbles may be released through the bubble release port. This bubble release port may be formed in a cap portion of the oxygenating apparatus. The oxygenating apparatus may also include an arrangement of fibers that facilitate fluid oxygenation. Other items, such as a heat exchanger, a hemoconcentrating device, a sampling device, or a pump, may be attached to the fluid oxygenating apparatus. The bubble release port may have a variety of structures including, but not limited to, a dome-like structure, a toroidal structure, or a helical structure.

Another aspect of the present invention provides a method of debubbling a fluid oxygenating apparatus. This method includes flowing fluid through an inlet end of a channel within the apparatus, collecting bubbles adjacent an outlet end of the channel, and releasing bubbles through the bubble release port. The method may include flowing the debubbled fluid through the fiber arrangement described above. The method may also include accumulating the bubbles in a structure such as a dome-like structure, a helical structure, or a toroidal structure. The method also provides for attaching such devices as a heat exchanger, a sampling device, a hemoconcentrator or a pump to the fluid oxygenating apparatus.

Another aspect of the present invention includes a fluid oxygenating apparatus with a housing that defines a chamber, a core positioned within the housing, a manifold formed within the core, a fiber bundle positioned around the core, and a bubble release port. The apparatus is arranged so that when bubbles accumulate in the apparatus as fluid flows through, the bubbles may be released through the port.

The foregoing, and other, features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims in equivalence thereof.

DETAILED DESCRIPTION OF THE PRESENTLY PREFERRED EMBODIMENTS

Figure 1:
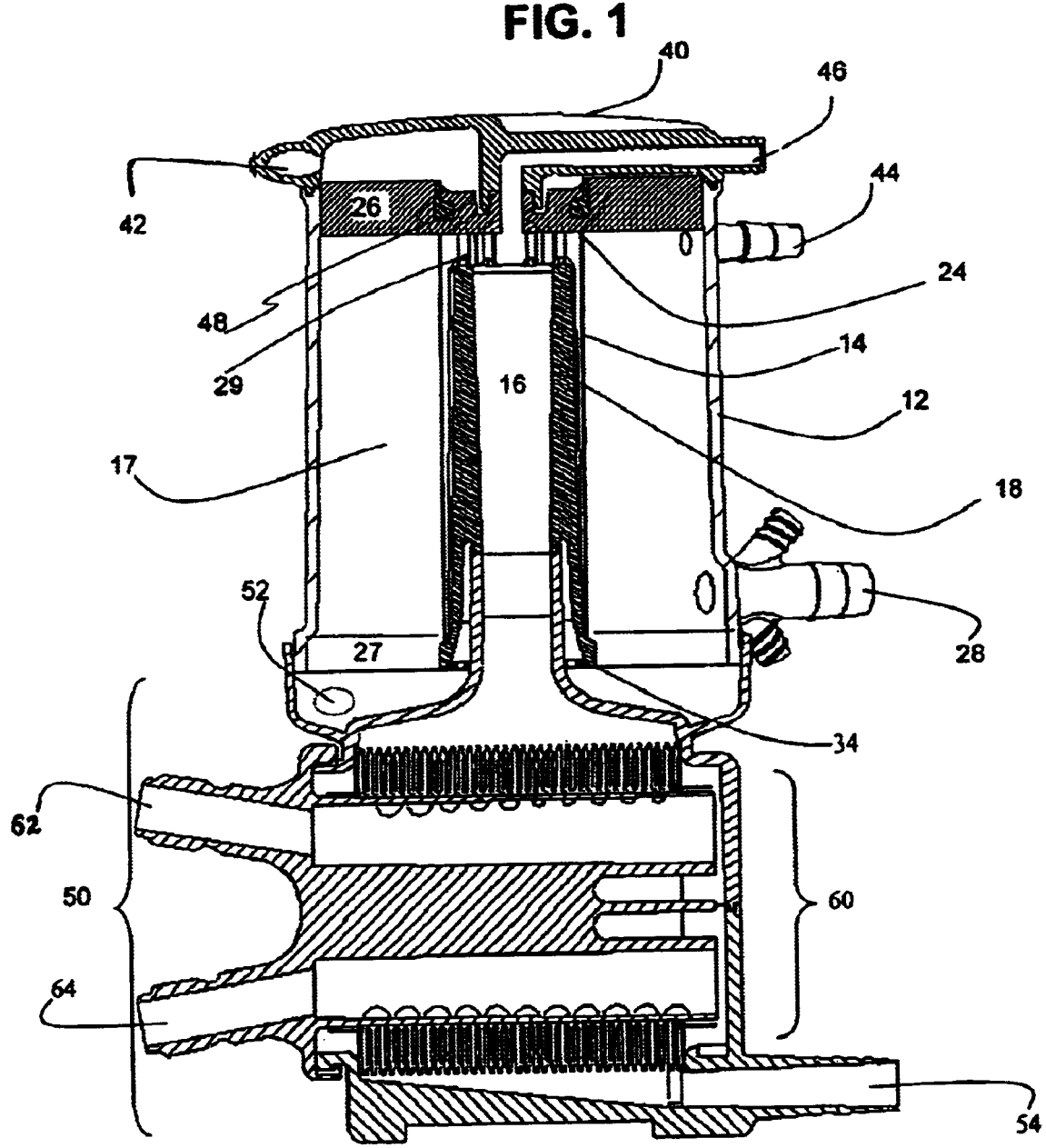
FIG. 1 is a cross-sectional view of a vertically oriented first embodiment of a fluid oxygenator in accordance with the present invention.

FIG. 1 illustrates a preferred embodiment of a blood oxygenator 10 in accordance with the present invention. Blood oxygenator 10 comprises a housing 12, which has a generally cylindrical outermost peripheral wall, open at both ends prior to assembly of the oxygenator 10. The housing 12 surrounds a core 14, which is also generally cylindrical. Within the core lies a manifold 16. A space 18 lies between the core and the manifold.

A fiber bundle 17 is wrapped around core 14. The fiber bundle 17 comprises a number of microporous fibers wound around the core 14. The core 14 has a first end, a second end and an axis extending from the first to the second end. The fiber bundle 17 extends radially outward relative to the axis of the core. Each of the fibers in the bundle 17 may preferably include a first end and a second end, a hollow interior and a semi-permeable wall. The fibers may also be coated with a biocompatible protein coat. Preferably the first ends of the fibers are adjacent the first end 24 of core 14 and the second ends of the fibers are adjacent the second end 34 of core 14.

Potting means 26, 27 are located at the end of said fibers. These potting means are typically adhesive means, for example a polyurethane adhesive, that seal the fibers. Potting means 26 are located adjacent the first end 24 of core 14 and preferably seal the first ends of the fibers. Potting means 27 are located adjacent the second end of core 14 and preferably seal the second ends of the fibers. Potting means 26, 27 also adhere to housing 12. Additionally potting means 26, 27 serve to separate the fluid phase from the gas phase within the oxygenator. A circumferential rib and window array 29 is located at the first end 24 of core 14.

A cap 40 is fitted at the top of the oxygenator 10 and generally includes a gas inlet 42. Cap 40 may be detachable from the oxygenator 10 or, as in the embodiment of FIG. 1 may be molded to oxygenator 10. A recirculation port 44 may be suitably located on oxygenator 10, for example, as seen in FIG. 1, adjacent cap 40 and through housing 12.

Figure 2:
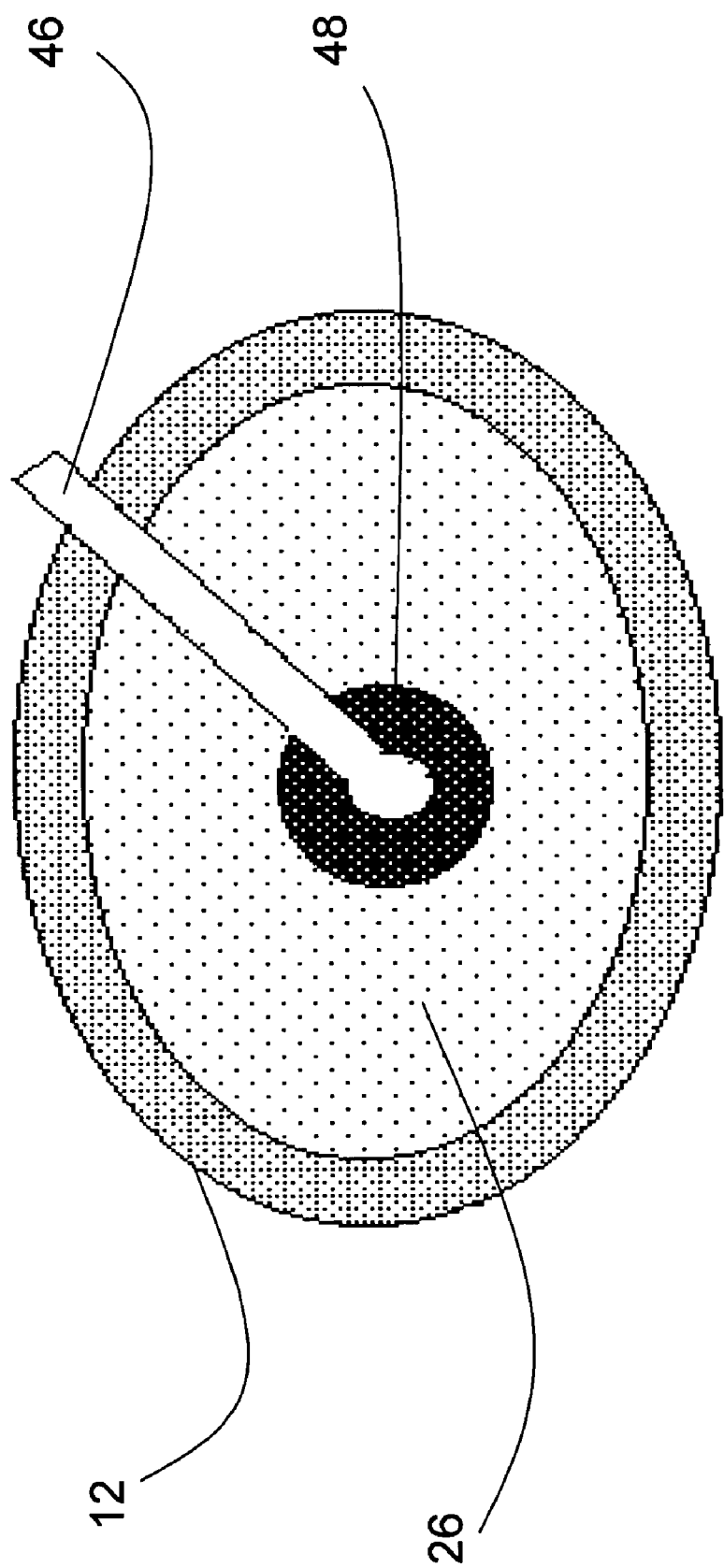
FIG. 2 is a top view of the fluid oxygenator of FIG. 1.

As shown in FIGS. 1 and 2, cap 40 also includes a bubble release port or access port 46. In one embodiment, access port 46 may be attached to the gas cap 40. In a second embodiment, the access port 46 is molded into gas cap 40. Alternatively, access port 46 may be a rigid or flexible tube or pathway that allows access to manifold 16 through the cap 40 or housing 12. When oxygenator 10 is in a typical vertical orientation, access port 46 allows access to the section of oxygenator 10 above potting means 26. Access port 46 may further allow access to the outer surface of core 14.

The gas cap 40 with access port 46 is mated to potting means 26, and thereby attached to oxygenator 10 as a whole, via mating feature 48.

Oxygenator 10 further includes a suitably located blood outlet 28. Outlet 28 may, as shown in FIG. 1 be located through housing 12 and adjacent the second end 34 of core 14.

The bottom of the oxygenator 10 is received in base 50. Base 50 includes gas outlet 52 and a suitably located blood entrance 54 for providing blood flow into oxygenator 10. It is contemplated that base 50 may be removably or permanently attached to the bottom of oxygenator 10.

Oxygenator 10 may also be attached to or carry a heat exchanger 60. A fluid type heat exchanger is depicted in FIG. 1 with an inlet 62 and an outlet 64, but other suitable heat exchange devices may be incorporated with oxygenator 10. In the embodiment shown in FIG. 1, for example, heat exchanger 60 is attached to oxygenator 10 and blood entrance 54 is incorporated into exchanger 60.

Oxygenator 10 may further be attached to other appropriate pumping or cooling or heating systems. Generally, a pumping system (not shown), such as, for example a peristaltic or centrifugal pump, is attached to oxygenator 10. Typically, oxygenator 10 is further attached to a reservoir, which provides blood to the oxygenator. The pumping system operates at sufficient pressure to send the blood from the reservoir, through the oxygenator 10 and eventually back to the patient. The value of this pressure is typically between 200 and 760 mm Hg, even more typically between 300 and 700 mm Hg although any pressure sufficient to send the blood on the above-described circuit is acceptable.

Figure 3:
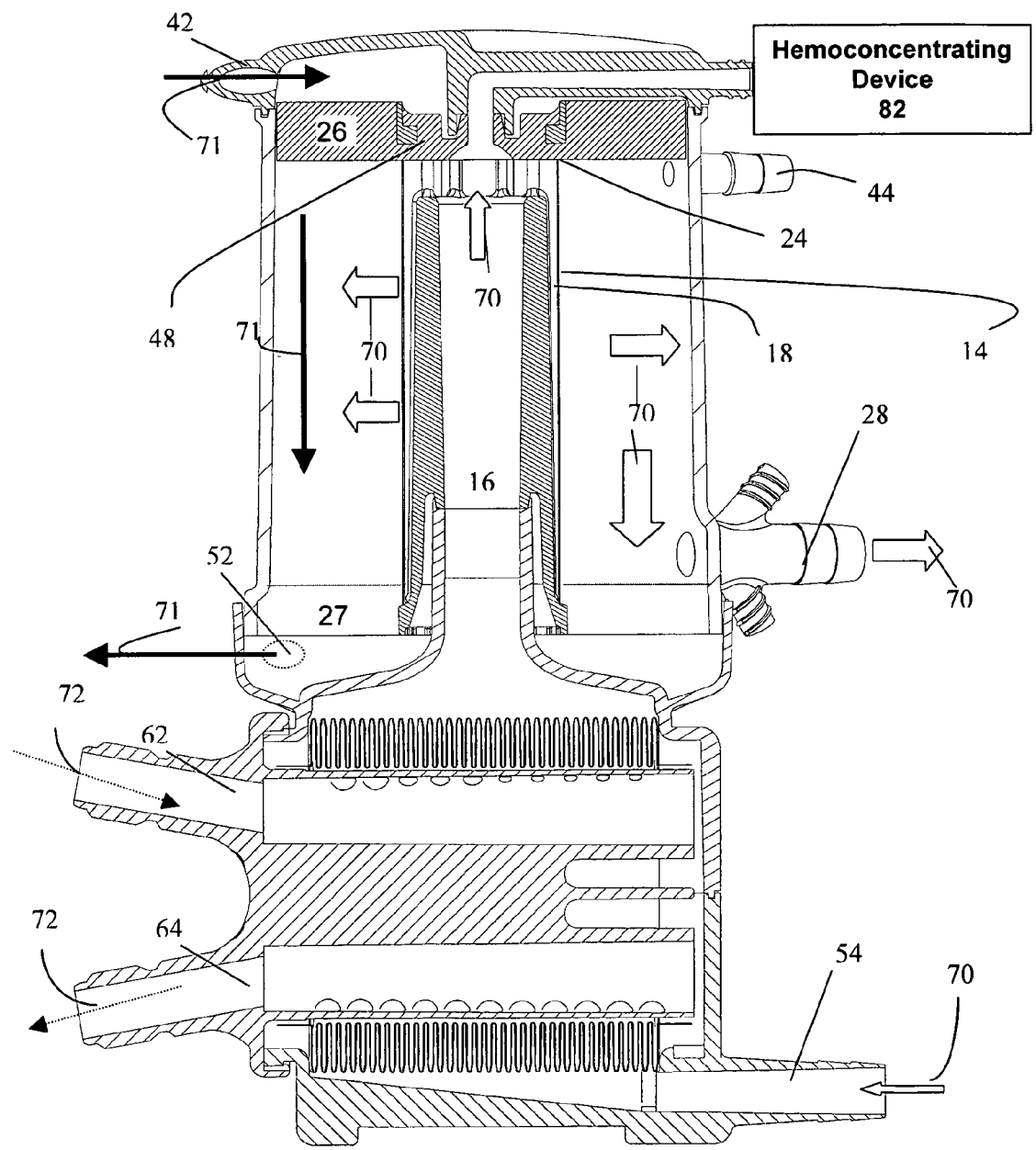
FIG. 3 is a cross-sectional view of the vertically oriented fluid oxygenator of FIG. 1 showing the flow of three different fluids through the oxygenator.

The oxygenator may be generally operated in a vertical position, such as that depicted in FIGS. 1 and 3. Referring to FIG. 3, the paths of three fluids, where fluid may be a liquid or gas, are illustrated. Solid white arrows 70 indicate the path of a fluid to be oxygenated, for example, blood. Solid black arrows 71 indicate the path of an oxygenating fluid, for example, oxygen. Dotted black arrows 72 indicate fluid in a heat exchanger, for example, water.

A fluid to be oxygenated, such as blood, is introduced into manifold 16 of the core 14 through the entrance 54 and flows up through manifold 16 toward the circumferential rib and window array 29 at the first end 24 of the core 14. This first end 24 is also where mating feature 48 meets potting means 26. The blood flows through the array 29 filling space 18 that surrounds an outer surface of the core 14.

From the manifold 16 the blood then flows radially away from the core 14, all along the length of the outer surface of the core 14 between upper potting means 26 and lower potting means 27.

The blood flows through the fiber bundle 17 and eventually exits the oxygenator 10 through the blood outlet 28. Fiber bundle 17 may be coated with a biocompatible protein coating. Fluid introduced into the oxygenator other than blood, such as priming fluid, will flow in the same manner described above.

Bubbles may be entrained in the fluid as it flows along this path. The bubbles are often carried from the blood reservoir or may form in the blood pump before it enters the blood inlet 54. Additionally, a priming fluid may be sent along the path before the blood is circulated through it. This priming fluid, typically a saline solution, may also carry bubbles from the reservoir or pump to the oxygenator inlet 54.

As the fluid flows through the fiber bundle 17, some of the bubbles may be unable to pass through the bundle 17. These bubbles accumulate within manifold 16 and core 14. These bubbles may block the blood flow path and may, if enough accumulate, retard the function of the oxygenator 10. Such accumulation of bubbles may occur particularly when the fibers are coated with a biocompatible material or coating.

The access port 46 allows access to manifold 16 and core 14 and provides means for debubbling the blood before it flows through the fiber bundle 17. In one typical method of operation, the pressure of the blood flowing through the oxygenator 10 is not sufficient to push blood out through access port 46. Rather, the pressure is just sufficient to send the blood flowing out of the array 29 at the top of core 14. The bubbles may tend to accumulate near this array 29, and elsewhere near the top of core 14, which brings them near the end of access port 46 that is mated to the core 14. From here, the bubbles may thus tend to disperse and may be released via the access port. The oxygenator 10 may be agitated to induce bubbles that accumulate in other areas of the flow path to move near the access port 46 and then be released. The access port allows the naturally buoyant bubbles a release path from the oxygenator 10.

In addition to providing this release path, access port 46 may also serve as a means to access the oxygenator 10 and the fluid flowing through the oxygenator while the oxygenator is in use. As seen in FIG. 3, this makes the fluid accessible before it passes through the fiber bundle 17.

As only one example, the access port 46 may be used as a blood supply site for a hemoconcentrator 82. A hemoconcentrator 82 may be attached to access port 46 so that the blood flows through the hemoconcentrating device 82. Additional pumping means may or may not be necessary to facilitate this additional flow. In a typical artificial circulation system, the hemoconcentrator is usually attached to recirculation port 44 of oxygenator 10. Additional attachment and pumping means (to provide sufficient pressure to move the blood through the hemoconcentrator 82) may be necessary in order for recirculation port 44 to continue its existing function and, at the same time, divert blood to the hemoconcentrator 82. However, when access port 46 is used as a blood supply port, an attached hemoconcentrator may rely on the already established pumping flow of oxygenator 10 as described above; this may eliminate the necessity for separate pumping means specific to the hemoconcentrator. Moreover, recirculation port 44 is left free to continue its recirculation function.

Figure 4:
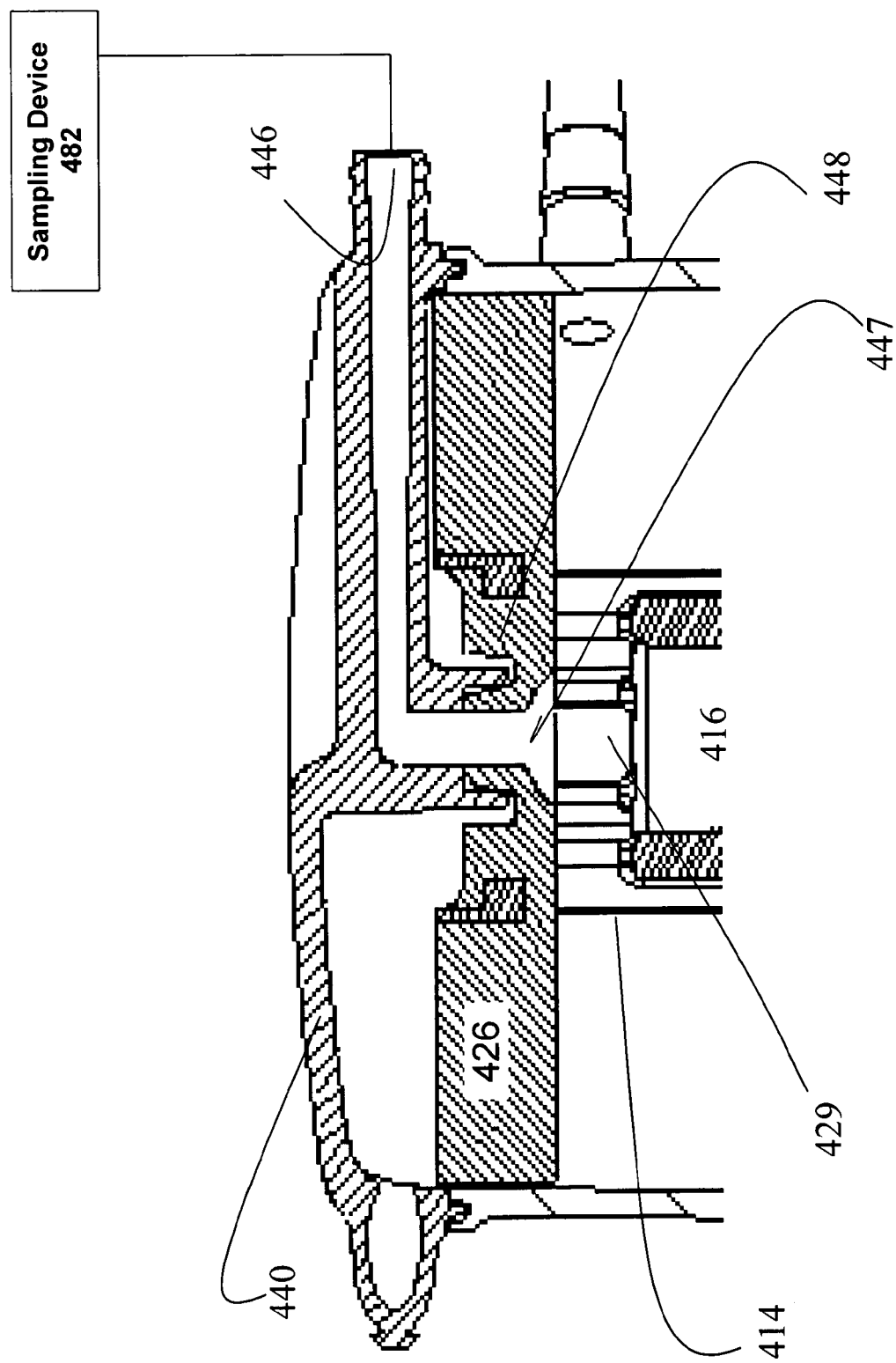
FIG. 4 is a partial cross-sectional view of a second embodiment of a fluid oxygenator in accordance with the present invention.

Occasionally, the blood flowing through the system is sampled. Usually, blood is sampled from the reservoir. Using access port 46 of the present invention, however, blood may be sampled as it is flowing through the oxygenator 10, thereby providing a more accurate sample. The same is true of pressure monitoring using access port 46 to monitor the blood in the manifold 16 and within the core 14. Any suitable sampling device 482, such as, for example, one that measures blood pressure or one which measure oxygenation levels, may be attached to access port 446 as indicated in FIG. 4.

Additionally, access port 46, if left open, can serve as a continuous purge port, providing a continuous means to purge air from the blood as it flows through the oxygenator 10.

Meanwhile, as shown in FIG. 3, a second fluid to provide oxygenation flows along the fluid path indicated by the solid black arrows 71. In this path, a gas, such as, for example, oxygen, enters the oxygenator 10 through the gas inlet 42 and flows into and through the hollow fibers comprising the bundle 17 and finally exits via the gas outlet 52. Gas exchange takes place via diffusion through micropores in the hollow fibers. This occurs as the blood is flowing radially through the fiber bundle 17 at the same time oxygen is flowing in a direction generally perpendicular to the blood.

If, as shown in FIG. 3, oxygenator 10 has an attached heat exchanger, a third fluid, such as water, flows along within a path in the heat exchanger 60 (designated by the dotted black arrows 72). This fluid enters at 62 and exits at 64 and heats or cools the blood as desired.

Referring again to FIG. 4, a second embodiment of access port 446 is shown. In this embodiment access port 446 is configured so that it has a dome-shaped attachment at end 447. In one embodiment, access port 446 may be attached to gas cap 440. In another embodiment, the port 446 is molded into gas cap 440. When the oxygenator is in a typical vertical orientation, access port 446 allows access to the section of the oxygenator above potting means 426. Access port 446 also allows access to manifold 416 within the core 414.

The gas cap 440 with attached port 446 is mated to potting means 426, and thereby attached to the oxygenator as a whole, via mating feature 448.

Debubbling occurs in the embodiment of FIG. 4 in a manner similar to that described above. The dome shape allows the bubbles to accumulate within or near the dome as they flow from the manifold 416 through rib and window array 429.

Figure 5:
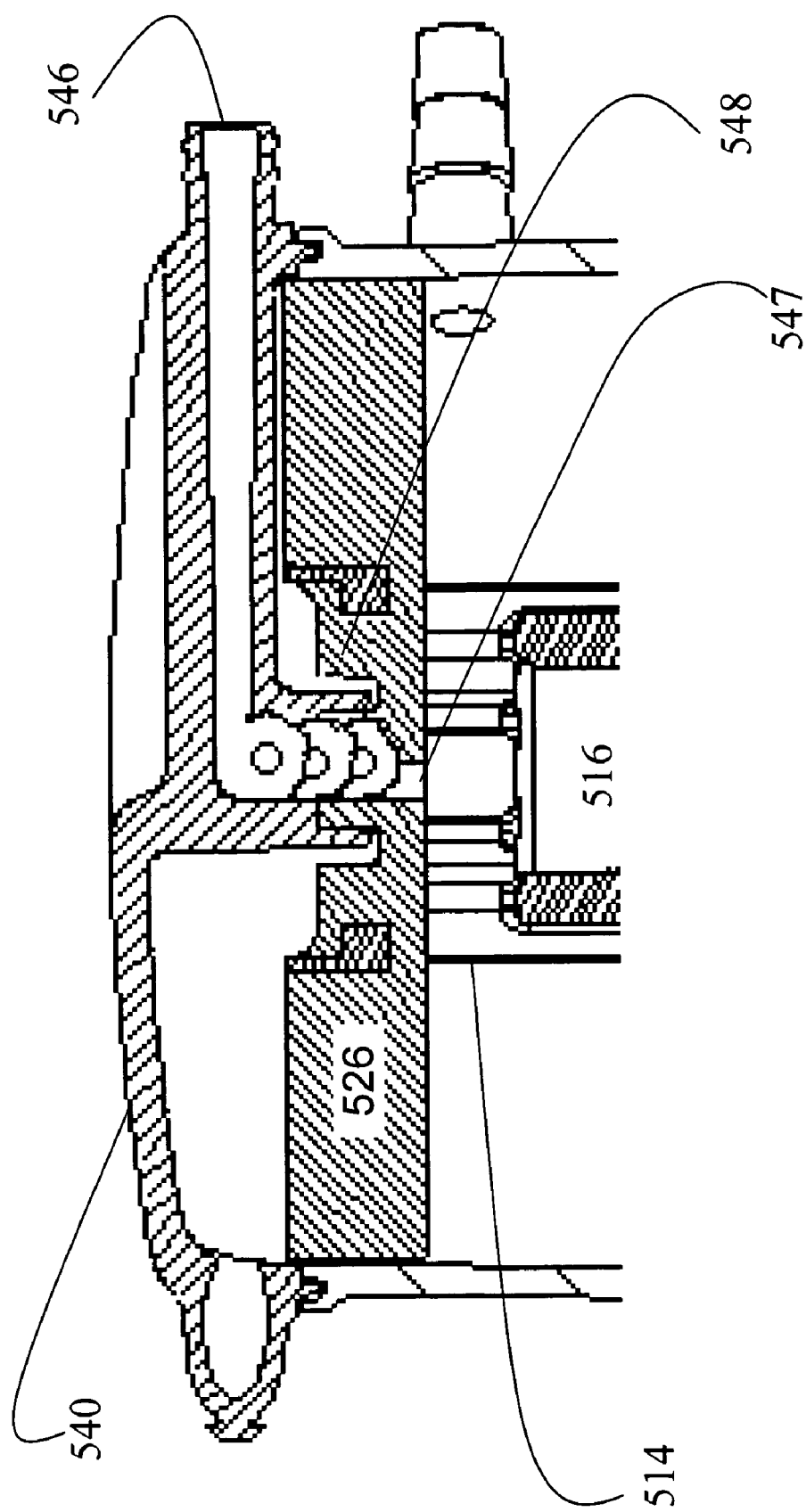
FIG. 5 is a partial cross-sectional view of a third embodiment of a fluid oxygenator in accordance with the present invention.

Referring to FIG. 5, a third embodiment of access port 546 is shown. In this embodiment access port 546 is configured so that it has a substantially toroidal or helical configuration at one end 547. It is contemplated that access port 546 may also be configured so that the entire port has a substantially toroidal or helical configuration. In one embodiment, access port 546 may be attached to gas cap 540. In another embodiment, the port 546 is molded into gas cap 540. When the oxygenator is in a typical vertical orientation, access port 546 allows access to the section of the oxygenator above potting means 526. Access port 546 also allows access the manifold 516 within the core 514.

The gas cap 540 with attached port 546 is mated to potting means 526, and thereby attached to the oxygenator as a whole, via mating feature 548.

Debubbling occurs in the embodiment of FIG. 3 in a manner similar to that described above. The toroidal or helical shape may facilitate entrapment of the bubbles.

It should be appreciated that the embodiments described above are to be considered in all respects only illustrative and not restrictive. The scope of the invention is indicated by the following claims rather than by the foregoing description. All changes that come within the meaning and range of equivalents are to be embraced within their scope.

We claim:

1. A fluid oxygenating apparatus comprising:
   a housing defining a chamber;
   a core positioned within and operatively attached to the housing, the core including a manifold formed therein, the manifold having an inlet at a bottom end and an outlet at a top end;
   a fiber bundle positioned around the core; and
   a bubble release port positioned between the fiber bundle and the top end of the manifold; wherein fluid is flowed through the inlet of the manifold and out the outlet of the manifold and through the fiber bundle and through an outlet in the housing while bubbles are released through the bubble release port prior to flowing through the fiber bundle.

2. A fluid oxygenating apparatus comprising:
   a housing, the housing comprising a fluid inlet and a fluid outlet;
   a core positioned within the housing, the core including a manifold formed therein, wherein the manifold includes an inlet at the bottom end of the manifold in fluid communication with the fluid inlet and an outlet at the top end of the manifold in fluid communication with the fluid outlet;
   a fiber bundle positioned around the core, the fiber bundle disposed between the outlet end of the manifold and the fluid outlet; and
   a bubble release, the bubble release disposed between the outlet end of the manifold and the fiber bundle, the bubble release in fluid communication with the outlet end of the manifold, wherein fluid is flowed through the fluid inlet, into the manifold at the inlet end, through the manifold and out the outlet end of the manifold, through the fiber bundle and out the fluid outlet, and bubbles are released through the bubble release port prior to passing through the fiber bundle.

3. The apparatus of claim 2 wherein the fiber bundle further comprises a plurality of fibers positioned in the housing and surrounding the core.

4. The apparatus of claim 3 further comprising a first potting element adjacent a first end of the fibers.

5. The apparatus of claim 4 further comprising a second potting element adjacent a second end of the fibers.

6. The apparatus of claim 5 wherein the housing includes a body portion and a cap portion, the bubble release port formed in the cap portion and the cap portion attached to the first potting means via a mating feature.

7. The apparatus of claim 3 wherein the fibers are coated with a biocompatible coating.

8. The apparatus of claim 7 wherein the biocompatible coating prevents the passage of bubbles through the fibers.

9. The apparatus of claim 2 wherein the housing includes a body portion and a cap portion, the bubble release port formed in the cap portion.

10. The apparatus of claim 9 wherein the cap portion is a separate member attached to the body portion.

11. The apparatus of claim 2 further comprising a heat exchanger operatively connected with the inlet end of the manifold, the heat exchanger including an inlet port to receive the fluid into the heat exchanger.

12. The apparatus of claim 2 wherein the bubble release port has a first end communicating with the outlet end of the manifold and a second end, further comprising:
a dome-like structure at the first end.

13. The apparatus of claim 2 wherein the bubble release port has a first end communicating with the outlet end of the manifold and a second end, further comprising:
a toroidal structure at the first end.

14. The apparatus of claim 2 wherein the bubble release port has a first end communicating with the outlet end of the manifold and a second end, further comprising:
a helical structure at the first end.

15. A method of debubbling a fluid oxygenating apparatus comprising:

providing a housing defining a chamber, a core positioned within and operatively attached to the housing, the core including a manifold formed therein, the manifold having an inlet at a bottom end and an outlet at a top end, a fiber bundle positioned around the core and a bubble release port positioned between the fiber bundle and the outlet end of the manifold and communicating with the outlet of the manifold;

flowing fluid through the inlet of the manifold and through the outlet of the manifold and through the fiber bundle and through an outlet in the housing;

collecting bubbles from the fluid adjacent the outlet of the manifold prior to the fluid flowing through the fiber bundle;

releasing the collected bubbles through the bubble release port; and oxygenating the fluid while flowing through the fiber bundle.

16. The method of claim 15 further comprising:
flowing the debubbled fluid through a plurality of fibers;
oxygenating the fluid as it passes through the fibers; and
flowing the fluid out a fluid outlet formed in the housing.

17. The method of claim 15 further comprising:
accumulating bubbles in a dome portion adjacent the outlet of the core.

18. The method of claim 15 further comprising:
accumulating bubbles in a helical portion adjacent the outlet of the core.

19. The method of claim 15 further comprising:
accumulating bubbles in a toroidal portion adjacent the outlet of the core.

20. The method of claim 15 further comprising:
providing a heat exchanger operatively connected with the inlet of the manifold, and flowing fluid through the heat exchanger.

* * * * *